US012688923B2

(12) United States Patent
Chen

(10) Patent No.: US 12,688,923 B2
(45) Date of Patent: Jul. 21, 2026

(54) PLAN OPTIMIZATION METHOD, COMPUTING APPARATUS USED FOR OPTIMIZING PLAN, AND COMPUTER-READABLE MEDIUM

(71) Applicant: Wistron Corporation, New Taipei City (TW)

(72) Inventor: Chih-Ming Chen, New Taipei City (TW)

(73) Assignee: Wistron Corporation, New Taipei City (TW)

( * ) Notice: Subject to any disclaimer, the term of this patent is extended or adjusted under 35 U.S.C. 154(b) by 276 days.

(21) Appl. No.: 18/434,789

(22) Filed: Feb. 6, 2024

(65) Prior Publication Data

US 2025/0226079 A1      Jul. 10, 2025

(30) Foreign Application Priority Data

Jan. 4, 2024     (TW) ................................. 113100329

(51) Int. Cl.
*G16H 20/40*          (2018.01)
*G16H 30/40*          (2018.01)
G16H 20/60          (2018.01)
(52) U.S. Cl.
CPC ............. *G16H 20/40* (2018.01); *G16H 30/40* (2018.01); *G16H 20/60* (2018.01)
(58) Field of Classification Search
CPC ........ G16H 20/10; G16H 20/30; G16H 20/40; G16H 20/60; G16H 20/70; G16H 20/90; G16H 30/40
See application file for complete search history.

(56) References Cited

U.S. PATENT DOCUMENTS

| | | | |
|---|---|---|---|
| 9,764,162 B1 | 9/2017 | Willcut et al. | |
| 11,132,615 B2 * | 9/2021 | Natarajan | G06N 20/00 |
| 2021/0220670 A1 | 7/2021 | Li et al. | |
| 2022/0076841 A1 * | 3/2022 | Abu El Ata | G16H 50/30 |
| 2022/0212034 A1 | 7/2022 | Ajdari et al. | |
| 2022/0367051 A1 * | 11/2022 | Mcgrath | G06N 3/045 |
| 2024/0104370 A1 * | 3/2024 | Ma | G16H 50/20 |
| 2024/0145090 A1 * | 5/2024 | Kano | G06N 7/01 |
| 2024/0321464 A1 * | 9/2024 | Gerner | G16H 50/70 |

FOREIGN PATENT DOCUMENTS

CN          116189881          5/2023

* cited by examiner

*Primary Examiner* — Mark R Gaworecki
(74) *Attorney, Agent, or Firm* — JCIPRNET

(57)          ABSTRACT

A plan optimization method, a computing apparatus for optimizing the plan, and a computer-readable medium are provided. Obtain multiple medical variables at the current time, at least one of the medical variables is different from the medical variables at the previous time, and one of those medical variables at the current time corresponds to a previous state at the previous time. By inputting those medical variables at the current time into the machine learning model, plan information is determined, where the plan information includes at least one subplan information, and each piece of subplan information corresponds to at least one treatment manner record at a subsequent time. Therefore, it could improve the inference accuracy of the model.

16 Claims, 6 Drawing Sheets

Obtaining multiple medical variables at the current time      ~S210

Determining plan information by inputting the medical variables at the current time into the machine learning model      ~S220

PLAN OPTIMIZATION METHOD, COMPUTING APPARATUS USED FOR OPTIMIZING PLAN, AND COMPUTER-READABLE MEDIUM

CROSS-REFERENCE TO RELATED APPLICATION

This application claims the priority benefit of Taiwan application serial no. 113100329, filed on Jan. 4, 2024. The entirety of the above-mentioned patent application is hereby incorporated by reference herein and made a part of this specification.

BACKGROUND

Technical Field

The disclosure relates to an optimization technology, and in particular relates to a plan optimization method, a computing apparatus used for optimizing a plan, and a computer-readable medium.

Description of Related Art

Radiation therapy, like other medical treatments, has some risks. However, these risks may be controlled and minimized through careful planning and implementation of treatment.

Manual radiation treatment planning may be time-consuming, which may not only lead to inconsistent treatment plans, but may also be prone to human error. Automated Radiotherapy Planning (ARP) may help reduce these errors and inconsistencies by using algorithms to optimize treatment plans, and may even help reduce the time required to develop a treatment plan. However, present day automated programs are not perfect and still require human oversight.

SUMMARY

A plan optimization method, a computing apparatus for optimizing the plan, and a computer-readable medium, which may improve the accuracy of a plan, are provided in the disclosure.

The plan optimization method of the disclosure includes (but not limited to) the following operation. Multiple medical variables are obtained at a current time, at least one of the medical variables is different from the medical variables at a previous time, and one of the medical variables at the current time corresponds to a previous state at the previous time. By inputting the medical variables at the current time into a machine learning model, plan information is determined, in which the plan information includes at least one subplan information, and each of the subplan information corresponds to at least one treatment manner record at a subsequent time.

The computing apparatus for optimizing the plan of the disclosure includes (but not limited to) a storage and a processor. The storage stores program code. The processor is coupled to the storage. The processor loads the program code and executes the following operation. Multiple medical variables are obtained at a current time, at least one of the medical variables is different from the medical variables at a previous time, and one of the medical variables at the current time corresponds to a previous state at the previous time. By inputting the medical variables at the current time into a machine learning model, plan information is determined, in which the plan information includes at least one subplan information, and each of the subplan information corresponds to at least one treatment manner record at a subsequent time.

The non-transitory computer-readable medium of the embodiment of the disclosure loads program code through a processor and executes the following operation. Multiple medical variables are obtained at a current time, at least one of the medical variables is different from the medical variables at a previous time, and one of the medical variables at the current time corresponds to a previous state at the previous time. By inputting the medical variables at the current time into a machine learning model, plan information is determined, in which the plan information includes at least one subplan information, and each of the subplan information corresponds to at least one treatment manner record at a subsequent time.

Based on the above, the plan optimization method, the computing apparatus for optimizing the plan, and the computer-readable medium of the embodiments of the disclosure may dynamically update medical parameters and change subsequent treatment manner records accordingly. In this way, the accuracy and reliability of the machine learning model may be improved.

In order to make the above-mentioned features and advantages of the disclosure comprehensible, embodiments accompanied with drawings are described in detail below.

DETAILED DESCRIPTION OF DISCLOSED EMBODIMENTS

Figure 1:
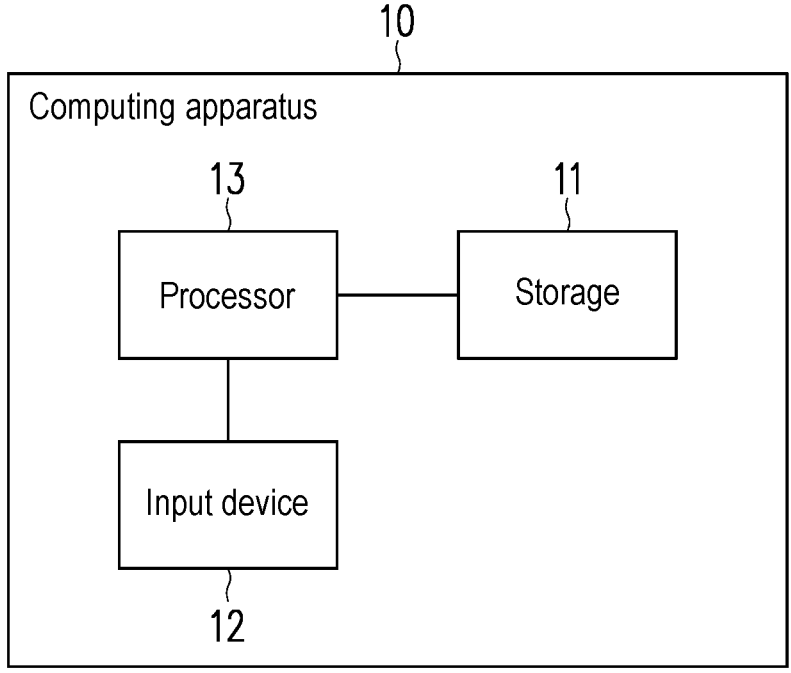
FIG. 1 is an element block diagram of a computing apparatus according to an embodiment of the disclosure.

FIG. 1 is an element block diagram of a computing apparatus 10 according to an embodiment of the disclosure. Referring to FIG. 1, the computing apparatus 10 includes (but is not limited to) a storage 11, an input device 12, and a processor 13. The computing apparatus 10 may be a computer host, a server, a smartphone, a tablet, a wearable device, a smart home appliance, a vehicle-mounted device, a medical assistance system, or other electronic devices.

The storage 11 may be any type of fixed or movable random access memory (RAM), read only memory (ROM), flash memory, conventional hard disk drive (HDD), solid-state drive (SSD) or similar components. In one embodiment, the storage 11 is configured to store program codes, software modules, configurations, data (e.g., machine learning parameters, medical variables, causal relationships, or time parameters) or files, and the embodiments thereof are described in detail below.

The input device 12 may be a microphone, a keyboard, a mouse, a touch panel, or a transmission interface (e.g., USB, Lightning, or communication transceiver). In one embodiment, the input device 12 is configured to obtain medical variables. Medical variables are described in detail in subsequent embodiments. For example, a user interface is provided and input of text, voice, image or other types of files is received through the input device 12.

The processor 13 is coupled to the storage 11 and the communication transceiver 12. The processor 13 may be a central processing unit (CPU), a graphics processing unit (GPU), or other programmable general-purpose or special-purpose microprocessors, a digital signal processor (DSP), a programmable controller, a field programmable gate array (FPGA), an application-specific integrated circuit (ASIC), a neural network accelerator, or other similar components, or combinations of components thereof. In one embodiment, the processor 13 is used to execute all or some of the operations of the computing apparatus 10, and may load and execute various program codes, software modules, files, and data stored in the storage device 11. In some embodiments, the functions of the processor 13 may be realized by software or chips.

Hereinafter, the method according to the embodiment of the disclosure is described in conjunction with various apparatuses, components, and modules in the computer apparatus 10. Each process of the method may be adjusted according to the implementation.

Figure 2:
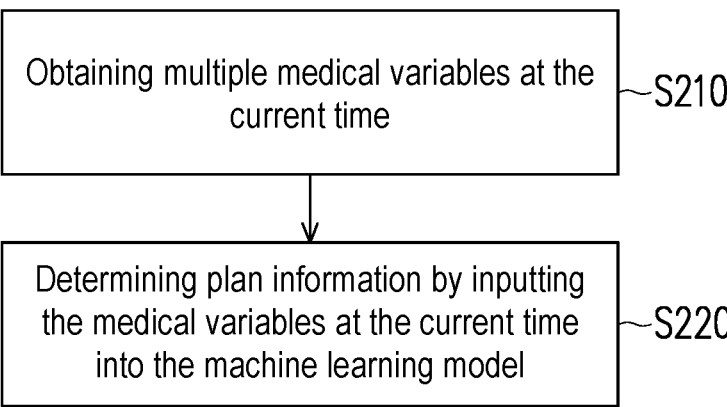
FIG. 2 is a flowchart of a plan optimization method according to an embodiment of the disclosure.

FIG. 2 is a flowchart of a plan optimization method according to an embodiment of the disclosure. Referring to FIG. 2, the processor 13 obtains multiple medical variables at the current time (step S210). Specifically, the current time may correspond to a time point or a time interval, and correspond to the current timing of execution of the processor 13, for example, today, this week, or this morning. However, the definitions of time points and time intervals may be different according to different design requirements, and may change depending on the user requirements.

On the other hand, medical variables may be specimen data, clinical data, medication records, operation records, test reports, consultation records, treatment records, emergency records, disease records and/or discharge/admission medical records. Patient-related variables may include identity (e.g., age or gender), medical history (e.g., prior treatments, surgeries, and pre-existing conditions), tumor features (e.g., location, size, stage, or pathology), and/or organ-at-risk (OAR) constraints (e.g., constraints or dose limitations on surrounding critical organs or normal tissue). Treatment-related variables may include treatment modality (e.g., selection of radiation modality), beam parameters (e.g., energy, intensity, incident angle, or beam shape), and/or dose prescription (e.g., irradiation dosage and dosage per irradiation). Image-related variables may include image features (e.g., resolution, imaging mode or quality), and/or segmentation/classification information (e.g., contour or volume). Taking the radiation treatment planning domain as an example, the state space may include variables such as the location and size of the tumor, the radiation dose delivered to the tumor and surrounding healthy tissue, and the overall health of the patient.

Regarding the application scenario of obtaining medical variables through the input device 12, for example, the user reads the content of the specimen data, the microphone receives the sound signal, and the sound signal may be converted into voice data (e.g., obtained through signal processing); for another example, the touch panel or keyboard receives input operations of surgical records; for another example, consultation records are obtained from a personal USB drive.

However, there are many types and/or acquisition methods of medical variables, and the embodiments of the disclosure are not limited thereto.

At least one of the medical variables at the current time is different from the medical variables at the previous time. The previous time is earlier than the current time. The previous time may correspond to a time point or a time interval, and correspond to the timing before the execution of the processor 13, for example, yesterday, last week, or last year. However, the definitions of time points and time intervals may be different according to different design requirements, and may change depending on the user requirements. Furthermore, one of the medical variables at the current time corresponds to a previous state at a previous time. The state belongs to a state space. The state space is formed of all possible combinations of values for the variables in the problem domain. Variables in the problem domain may include factors related to the patient, treatment, and imaging data, for example, the aforementioned medical variables. That is, the state includes one or more medical variables. The previous state is, for example, medical images taken last week, yesterday, or in the morning, and/or details of the previous treatment manner record, but not limited thereto.

Figure 3:
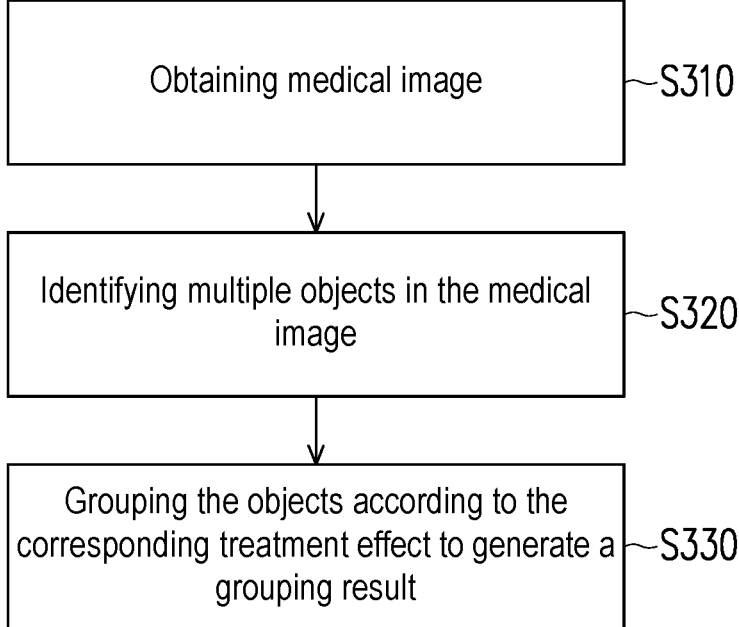
FIG. 3 is a flowchart of a generation method of medical variables according to an embodiment of the disclosure.

FIG. 3 is a flowchart of a generation method of medical variables according to an embodiment of the disclosure. Referring to FIG. 3, the processor 13 may obtain one or more medical images (step S310). Specifically, medical images may be generated through computed tomography, magnetic resonance imaging or other imaging methods. For the method of obtaining medical images, reference may be made to the aforementioned method of obtaining medical variables, which are not repeated herein.

The processor 13 may identify multiple objects in the medical image (step S320).

Specifically, the processor 13 may identify the type and/or location/contour of structured objects through algorithms based on semantic segmentation (e.g., RefineNet, SegNet, or PSPNet), algorithms based on neural network (e.g., you only look once (YOLO)), region-based convolutional neural networks (R-CNN), fast R-CNN (fast CNN), or feature comparison based on feature matching algorithm (e.g., histogram of oriented gradient (HOG), scale-invariant feature transform (SIFT), Harr, or speeded up robust features (SURF)).

In some of the above algorithms, target objects (e.g., tumors or tissues) in training samples may be marked, and the marked training samples may be used to train machine learning related models (e.g., semantic segmentation models or CNN models). In this way, objects in medical images may be inferred through trained machine learning models. For example, the type of object and its contour or the occupied image region may be marked.

In one embodiment, the processor 13 may perform resizing, scaling, normalizing pixel intensity or other image preprocessing on the medical image. In one embodiment, the processor 13 may perform noise reduction, smoothing or morphological operations on the medical image, thereby improving the accuracy and quality of semantic segmentation or object recognition.

In one embodiment, the results of semantic segmentation or object recognition may serve as medical variables.

The processor 13 may group the objects according to their corresponding treatment effects to generate a grouping result (step S330). Specifically, objects with similar or identical treatment effects are assigned to the same group. The grouping result is one or more groups, and the corresponding treatment effects of multiple objects in each group are the same or similar.

In one embodiment, the processor 13 may estimate the treatment effect corresponding to each object. Causal segmentation may be configured to identify groups of semantic segments (e.g., regions or structures) in medical images, and these groups exhibit different treatment effects based on their estimated causal effects. By applying causal inference techniques to each segment, groups with different responses to treatments or interventions may be identified. For example, the processor 13 may estimate the conditional average treatment effect (CATE) through Bayesian structural equation modeling (BSEM), and the conditional average treatment effect is the treatment effect corresponding to a certain object. In the context of causal segmentation, Bayesian structural equation modeling may be configured to specify a causal model that represents the relationship between treatment, result variables, and other relevant variables in each segment. In addition, the model may capture causal pathways and dependencies between variables, so that the treatment effect may be estimated. As another example, a propensity score matching algorithm may match individuals who receive treatment with those who do not according to the predicted probability of receiving treatment. As another example, the instrumental variables algorithm may estimate the causal effect of a treatment using instrumental variables that are related to the treatment but not directly related to the result. For example, a regression discontinuity design compares individuals above and below a treatment threshold.

The processor 13 may group the estimated treatment effects into groups through a grouping algorithm. The grouping algorithm (also known as the clustering algorithm) may be k-means algorithm (K-means), Gaussian mixture model (GMM), clustering algorithm (mean-shift), hierarchical grouping method, spectral grouping algorithm, density-based spatial clustering of applications with noise (DB-SCAN) algorithm or other grouping algorithms. Grouping algorithms may classify treatment effects and group similar or identical treatment effects into the same group.

In addition, medical variables include a grouping result. That is, the object grouping result serves as one of the medical variables. In some application scenarios, providing corresponding intervention measures or treatment methods for specific groups may meet customized requirements and provide effective medical intervention. Therefore, the grouping result may be configured to optimize treatment planning.

Referring to FIG. 2, the processor 13 determines plan information by inputting multiple medical variables at the current time into the machine learning model (step S230, not shown). Specifically, the plan information includes one or more subplan information, each subplan information corresponds to one or more treatment manner records at a subsequent time, and the subsequent time is later than the current time. The subsequent time may correspond to a time point or a time interval, and correspond to the timing after the processor 13 is executed, for example, tomorrow, next week, or this afternoon. However, the definitions of time points and time intervals may be different according to different design requirements, and may change depending on the user requirements. For another example, the plan information includes three subplan information, and these three subplan information respectively correspond to the subsequent time of one month later, three months later, and six months later.

Different types of treatment manner records may involve different tool types, dosages, quantities, directions and other parameters. Taking radiotherapy as an example, the content includes the target region (e.g., the specific anatomical region or location and range of the tumor for radiotherapy), the radiation dose, and treatment techniques (e.g., external beam radiotherapy, brachytherapy, or other combinations of techniques); the timing includes the treatment schedule (e.g., frequency and duration of treatment); the treatment modality: for example, photon therapy (X-rays or gamma rays) or particle therapy (proton or carbon ion therapy); treatment implementation parameters: the prescription provides instructions on how to implement the radiation, including the energy and intensity of the radiation beam, the incident angle of the radiation beam, and any other treatment parameters specific to the chosen technique; organ constraints: the prescription may include constraints or dose limitations on critical organs or normal tissues surrounding the target region to ensure that their tolerance is not exceeded during the treatment process.

In addition, among the various treatment methods for specific lesions, different treatment manner records (involving parameters such as tool type, dose, quantity, direction) may lead to different treatment effects. Generally speaking, it requires reliance on medical professionals for decision-making, and the overall plan for specific patients is fixed and unchangeable. For example, the subplans corresponding to different time points in the plan are decided at the beginning and will not be changed. However, the state may change at subsequent time points. For example, changes in tumor size or location, changes in patient anatomy, equipment issues, patient compliance, acute side effects, or emergencies leading to changed state.

In an embodiment of the disclosure, the plan information corresponding to the medical variables at the current time (corresponding to the previous state at the previous time) may be inferred through the machine learning model, and the subplan information corresponding to the subsequent time may be changed accordingly. That is, the treatment manner records at subsequent times are dynamically change throughout the continuous time. The machine learning model is trained to understand the correlation between input samples (e.g., medical variables) and output results (e.g., the contents of one or more plan information/treatment manner records). The machine learning model is, for example, a causal graph model, a CNN model, an RNN model or other models.

In some application scenarios, one piece of plan information includes multiple pieces of subplan information. That is, they correspond to treatment manner records of multiple subsequent times, for example, treatment manner records of six months later, one year later, and two years later. The implementation of treatment manner record will affect the treatment effect.

Figure 4:
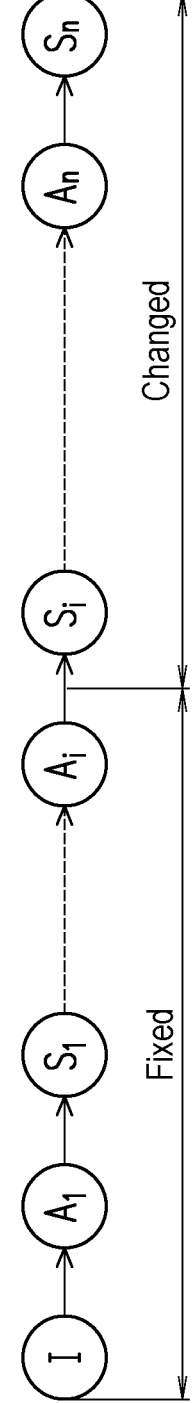
FIG. 4 is a schematic diagram illustrating subplan information according to an embodiment of the disclosure.

FIG. 4 is a schematic diagram illustrating subplan information according to an embodiment of the disclosure. Referring to FIG. 4, the initial state I may be regarded as the previous state at a previous time. The action node $A_1$ is the action node corresponding to the first time, and the action node is configured to execute the inference of the machine learning model. For example, the corresponding treatment manner record is determined according to medical variables. In addition, the state node $S_1$ is the state node corresponding to the first time. This state node corresponds to the state obtained after implementing the treatment manner record in the subplan information determined by the action node $A_1$. By analogy, the action node $A_i$ is the action node corresponding to the $i^{th}$ time (after the first time, corresponding to the aforementioned current time, and i is a positive integer), the action node $A_n$ is the action node corresponding to the $n^{th}$ time (after the $i^{th}$ time, corresponding to the aforementioned subsequent time, and n is a positive integer greater than i), the state node $S^i$ is the state node corresponding to the $i^{th}$ time, and the state node Sn is the state node corresponding to the $n^{th}$ time.

The $i^{th}$ time may be any time point in the continuous time. Even if subplan information (fixed) of all subsequent times are determined by using action node $A_1$ before the $i^{th}$ time, the replanning of the action node $A_i$ at the $i^{th}$ time may change the subplan information at subsequent times. The processor 13 may only modify the remaining subplan information in the plan information to respond to environmental changes or unexpected events while still achieving the original goals of the plan. For example, in FIG. 4, the action node $A_i$ changes state. The sub-path from the initial state I to the action node $A_i$ is fixed, but the sub-path from the state node $S^i$ to the state node Sn changes.

In one embodiment, the machine learning model is a causal graph model. The processor 13 may determine the causal relationships corresponding to multiple medical variables at the current time through the causal graph model. A causal graph is a graph structure expression formed of causal relationships. The causal relationships represent the causality from the first variable to the second variable. For example, the second variable is caused by the implementation of the first variable, but not limited thereto. In response to at least one of the medical variables at the current time being different from the medical variables at the previous time (e.g., environmental changes or unexpected events leading to state transitions), the processor 13 may generate a causal relationship different from that corresponding to the previous time through the causal graph model, and accordingly change the treatment manner record in one or more subplan information corresponding to the previous time. In other words, even if the subplan information corresponding to one or more subsequent times has been determined at a previous time point, the causal relationship between medical variables may be changed through inference according to the medical variables at the current time (which may be affected by environmental changes or other events) through the causal graph model, thereby affecting the causal relationship corresponding to the subplan information at subsequent times. The aforementioned way of changing the causal relationship over time may be referred to as a continuous time dynamic causal planning graph (CTDCPG).

Figure 5:
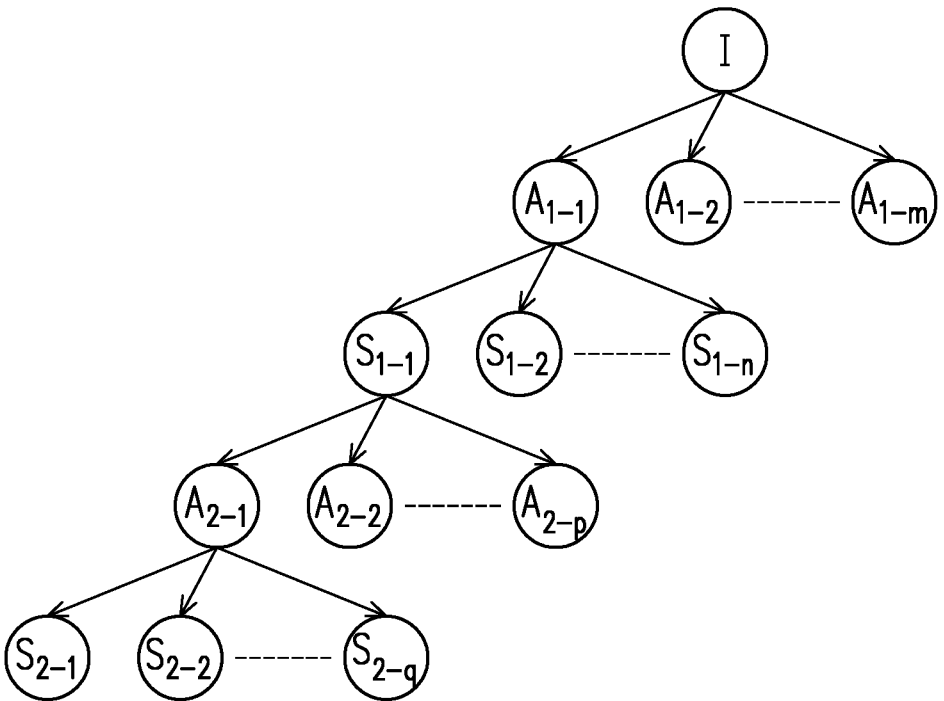
FIG. 5 is a schematic diagram illustrating the generation of subplan information according to an embodiment of the disclosure.

For example, FIG. 5 is a schematic diagram illustrating the generation of subplan information according to an embodiment of the disclosure. Referring to FIG. 5, the causal graph model may take into account the current state of the causal graph and the available actions (e.g., treatment manner), and choose actions that may lead to the desired state. Next, the causal graph is updated to reflect the effect of the selected actions on the medical variables in the problem domain. This process continues until the causal graph reaches a state where the desired goal or purpose is met. For example, in the radiation treatment planning domain, the state space may include medical variables such as the location and size of the tumor, the radiation dose delivered to the tumor and surrounding healthy tissue, and the overall health of the patient. Each state node $S_{1-1}$ to $S_{1-n}$ and $S_{2-1}$ to $S_{1-4}$ in the drawing represents a specific value combination of these medical variables. The state nodes $S_{1-1}$ to $S_{1-n}$ (n is a positive integer) correspond to the n treatment manner records of the subplan information determined by the action node $A_{1-1}$ at the first time. By analogy, each action node $A_{1-2}$ to $A_{1-m}$ (m is a positive integer) has its own state nodes corresponding to multiple treatment manner records. The state nodes $S_{2-1}$ to $S_{2-4}$ (q is a positive integer) correspond to the n treatment manner records of the subplan information determined by the action node $A_{2-1}$ at the second time. By analogy, each action node $A_{2-2}$ to $A_{2-p}$ (p is a positive integer) has its own state nodes corresponding to multiple treatment manner records.

Finding treatment manner record/subprogram information often involves determining a set of interventions that may achieve the desired results. The processor 13 may use various search algorithms to search for treatment manner record/subplan information. In one embodiment, the processor 13 uses an exhaustive search as the search algorithm to ensure that the best solution is found. The working principle of this algorithm is to consider all possible combinations of states and transitions, and accordingly select the combination that generates the best results (including subplan information for one or more subsequent times).

Furthermore, the decision of the best result/solution is related to the objective function of the path. In one embodiment, the processor 13 may define multi-objective functions (problems involving corresponding objectives). The objective function may be a composite metric that combines different metrics (e.g., tumor control, minimization of side effects, treatment time, or resource utilization). The specific formulation of the objective function depends on the goals and priorities of the automated treatment planning system and the specific requirements of the treatment process.

States may change not only due to exogenous factors, but also due to interventions or actions taken. Therefore, the time between state transitions depends not only on the underlying stochastic process but also on the timing of the intervention.

Figure 6:
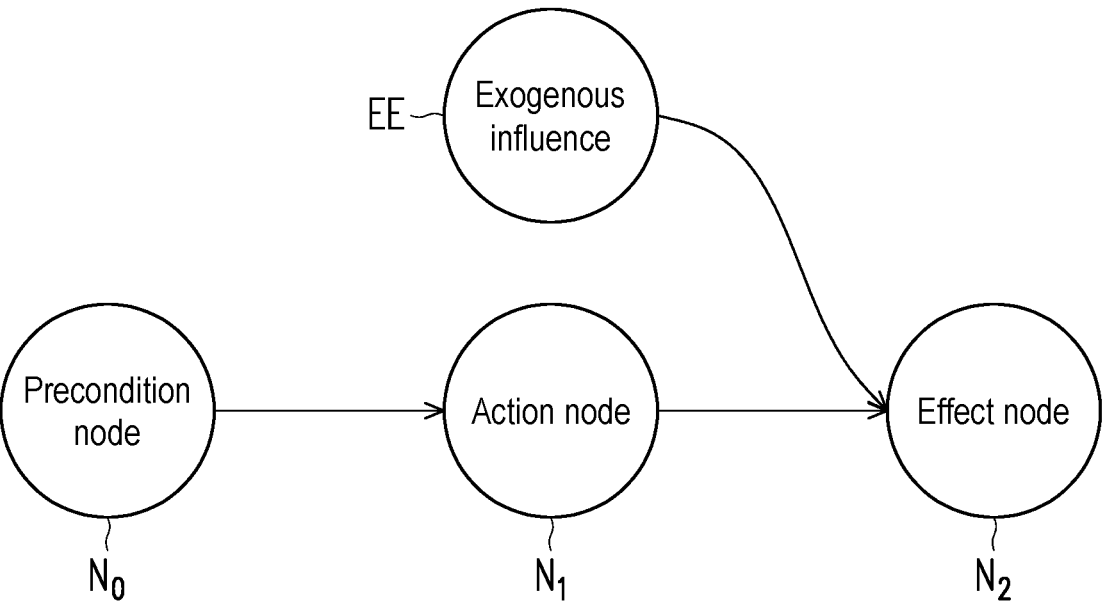
FIG. 6 is a schematic diagram illustrating timing relationships according to an embodiment of the disclosure.
Figure 6:
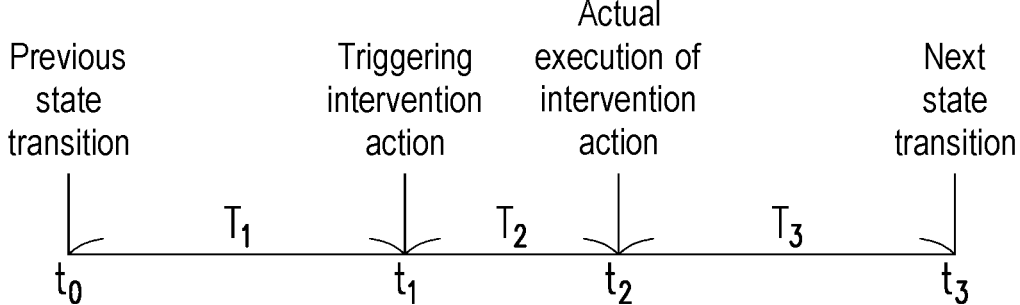

FIG. 6 is a schematic diagram illustrating timing relationships according to an embodiment of the disclosure. Referring to FIG. 6, the processor 13 may set the first period $T_1$ as the first probability distribution. The first period $T_1$ is a period between the time point to of the precondition node $N_0$ and the time point $t_1$ of the action node $N_1$. The precondition node $N_0$ corresponds to the input of the previous state. This previous state is the last state transition relative to the current time and corresponds to the initial state or the state after implementation of a specific treatment manner, for example, a health report from a first medical visit of a patient. The action node $N_1$ is configured to trigger the intervention behavior of the causal relationships corresponding to multiple medical variables at the current time, and the intervention behavior changes the causal relationship corresponding to those medical variables through the causal graph model. For example, the intervention behavior blocks, adds or changes the causal relationship and starts the selected action node accordingly.

It is assumed that there is a constant amount of time $T_1$ between the last state transition (e.g., at precondition node $N_0$) and the intervention behavior/function initiation (at action node $N_1$). In one embodiment, the probability density function (PDF) of the first period $T_1$ may be expressed as a Dirac (delta) distribution (e.g., the first probability distribution):

$$f1(T_1) = \delta(T_1 - t), \tag{1}$$

where $f_1 (T_1)$ is the probability density function of the first period $T_1$ and t is a specific constant time value between the last state transition (e.g., preconditioned node $N_0$) and the intervention (e.g., action node $N_1$). The delta distribution represents a probability density function that is non-zero only at specific values of t and is zero elsewhere. In one embodiment, the processor 13 sets the first period $T_1$ to a fixed constant.

The processor 13 may set that the second period $T_2$ corresponding to the current time belongs to the second probability distribution. The second period $T_2$ is the delay of the intervention behavior and corresponds to the period from the time point $t_1$ when the intervention behavior is triggered to the time point $t_2$ when the intervention behavior is actually executed. The delay distribution of action node $N_1$ itself depends on the intervention function/behavior and the specific implementation and features of action node $N_1$. The second period $T_2$ may vary depending on factors such as computing time, processing speed, and the complexity of determining the treatment plan. In one embodiment, the second period $T_2$ is, for example, a normal distribution or a uniform distribution, or even a customized distribution based on empirical data or professional knowledge. In one embodiment, the second period $T_2$ belongs to a gamma distribution.

The processor 13 may set the third period $T_3$ to belong to the third probability distribution. The third period $T_3$ is the period between the time point $t_2$ of the action node $N_1$ and the time point $t_3$ of the effect node $N_2$. Furthermore, the effect node $N_2$ corresponds to the input of the new state at the current time. This new state is relative to the next state transition when the intervention behavior of the action node $N_1$ is implemented and/or the causal relationship/subplan information is changed, and corresponds to the state after the specific treatment manner decided by the action node $N_1$ is implemented. In some application scenarios, exogenous influence EE (e.g., event occurrence or environmental change) leads to a new state. The time point $t_3$ of the time point of effect node $N_2$ refers to the time when the treatment effect or response is reviewed or evaluated. It represents the moment when the results or effects of an intervention behavior/function are observed or measured. It may be a specific time point during or after the treatment session at which the state transition of effect node $N_2$ occurs. By determining the time point $t_3$ of the effect node $N_2$, the timing and effectiveness of the treatment intervention may be understood.

In one embodiment, the third period $T_3$ belongs to exponential distribution. This distribution depends on the time since the last intervention behavior. The mathematical expression is:

$$f2(T_2) = \lambda e^{\wedge}(-\lambda T_3), \quad (2)$$

where $\lambda$ is the parameter of the decay rate of the intervention interval, and $T_3$ is the time elapsed since the last intervention behavior. Based on this distribution, it may be seen that the longer the time since the last intervention behavior, the greater the possibility of a state transition. Parameters of an exponential distribution, such as the rate parameter that determines the shape of the distribution, may be estimated from the data using statistical methods. For causal graph models for automated treatment planning, rate parameters may be estimated from historical data on patient response times to treatment interventions. "Patient response time to treatment intervention" refers to the duration of time from when the patient receives the treatment intervention to when the patient shows a response to this treatment intervention. This may include the time between when the patient receives radiation therapy and when the tumor begins to shrink. Alternatively, domain experts may use their knowledge and expertise to set the rate parameters according to previous experience and research results. However, the method of parameter estimation still depends on the specific application and the available data and resources.

In one embodiment, the aforementioned probability distribution may be estimated according to the historical data of the patient. For example, assuming a patient has a tumor near a critical organ, the treatment plan involves administering small doses of radiation therapy over several weeks. In this scenario, a fixed delay (e.g., the aforementioned first period) may be set to a few days between treatments to allow the body of the patient to recover and minimize the risk of complications. The gamma distribution may be configured to model the time between intervention behaviors, with rate parameters estimated according to historical data on patient response times to treatment interventions. The exponential distribution may be configured to model the time elapsed since the last intervention behavior and estimate the rate parameter according to the same data. In one embodiment, statistical methods may be used to estimate parameters of gamma and exponential distributions, which may enhance the accuracy of period estimation.

Compared to human-determination of the aforementioned periods, embodiments of the disclosure may improve the accuracy and efficiency of model inference. For example, human decision-makers may not have access to patient response data or may not be able to accurately estimate the appropriate period between treatment interventions according to the changing condition of the patient. However, embodiments of the disclosure may accurately estimate the time point of each node, in order to enter state, execute intervention behaviors, or decide on subplan information at the appropriate time. For example, assuming a cancer patient receives radiation therapy, a human decision-maker determines that the interval between two treatment courses is two weeks. However, the response of the patient to treatment varies significantly over time, and the condition may improve or worsen during treatment. In this scenario, the human-determined time interval may not be optimal, making it difficult to estimate accurate subplan information and preventing the patient from receiving the most effective treatment. In contrast, embodiments of the disclosure use statistical methods to estimate the period between nodes, which may enhance the accuracy of time interval estimation, improve the accuracy of model estimation, and may reflect exogenous influences in a timely manner.

In one embodiment, the processor 13 may set an intensity matrix. This intensity matrix corresponds to the probability of the state transition of the effect node. The input of the previous state (e.g., the precondition node $N_0$ of FIG. 6) or the input of the new state at the current time (e.g., the effect node $N_2$ of FIG. 6) corresponds to the state transition. Each of the plurality of elements of the intensity matrix corresponds to an instantaneous rate of state transition of two states.

The intensity matrix represented by Q is a square matrix, where the (i, j)th unit element represents the instantaneous rate at which the system transitions from state i to state j. The diagonal elements of the intensity matrix represent the instantaneous rate at which the system remains in the same state. The intensity matrix depends on the corresponding probability distribution for the third period and may be configured to define the structural equation of the causal graph model.

In one embodiment, the instantaneous rate of one or more elements in the intensity matrix corresponding to a state transition in which the previous state is the first state corresponds to a period belonging to a certain probability distribution. The instantaneous rate of one or more elements in the intensity matrix corresponding to a state transition in which the previous state is the second state corresponds to a transition to a new state without executing an intervention behavior. The instantaneous rate of one or more elements in the intensity matrix corresponding to a state transition in which the previous state is the third state corresponds to state maintenance without executing an intervention behavior.

For example, it is assumed that there are three variables: X1, A, and X2, where X1 and X2 respectively represent the system state before and after the intervention behavior (corresponding to one or more medical variables), and A represents the time point of the intervention behavior. For example, variable X2 represents the concentration of a reactant, and external factors such as changes in temperature or pressure may cause variable X2 to change its state. Similarly, the presence of other reactants or catalysts may also affect the reaction rate. Inhibitors or activators may also affect the reaction rate by respectively slowing down or speeding up the reaction. Finally, the pH of a solution may also affect the reaction rate by changing the chemical properties of the reactants. These external factors may be regarded as exogenous influences.

Assuming that the second period between the intervention behavior and the state transition of state X2 follows the exponential distribution of the rate parameter $\lambda$, the intensity matrix Q may be defined as:

$$Q = \begin{bmatrix} Q11 & Q12 & Q13 \\ 0 & Q22 & Q23 \\ 0 & 0 & Q33 \end{bmatrix}, \tag{3}$$

where element Q11=$-\lambda$, element Q12=$\lambda$, element Q13=0, element Q22=$-\mu$, element Q23=$\mu$, and Q33=$-v$. The transition probability from the state corresponding to element Q11 to the state corresponding to element Q12 is $\lambda/\lambda$=1.2 represents the time occurrence rate between the intervention behavior and the state transition of state X2. For example, $\lambda$=0.1. Furthermore, since the time between the last state transition and the intervention behavior has occurred, the system must have transitioned to the state corresponding to element Q12. Here, u is the instantaneous rate at which variable X2 transitions to a new state without intervention behavior, and v is the instantaneous rate at which variable X2 remains in the same state without intervention behavior. For example, u is 0.2 and v is 0.3. The element Q23 represents the rate at which variable X2 transitions from state 2 to state 3 due to some other exogenous influence (not from state X1 or A). Therefore, the second row sums to zero and represents the total rate of leaving state 2, regardless of exogenous influence. However, if the rate at which variable X2 transitions from state 2 to the new state is not uniformly distributed, the sum of the second row may be non-zero. Since variable X2 may only transition to a new state through an intervention variable A, there is no direct transition from variable X1 to variable X2 without an intervention behavior. Therefore, the diagonal element of the third row (corresponding to element Q33) represents the rate at which variable X2 remains in the same state without any influence from variable X1 or variable A. Therefore, the third row does not need to sum to zero.

The off-diagonal elements in the first row of the intensity matrix Q (i.e., elements Q12, Q13) reflect the fact that intervention behaviors may cause the system to transition from state 1 to state 2 or state 3, depending on the value of variable A. Therefore, the sum of the off-diagonal elements in the first row of the intensity matrix Q is not necessarily zero. The off-diagonal elements of the second row of the intensity matrix Q (i.e., element Q23) reflect the instantaneous rate at which the variable X2 transitions to a new state after the intervention behavior. Furthermore, the diagonal elements of the intensity matrix Q represent the instantaneous rate at which the system maintains each state.

In one embodiment, the processor 13 may train a causal graph model through a continuous time structural equation model (CTSEM), and determine the causal relationship corresponding to the precondition node and the action node, or the causal relationship corresponding to the action node and the effect node. Taking FIG. 6 as an example, the precondition node $N_0$ corresponds to the input of the previous state, the action node $N_1$ is configured to trigger the intervention behavior of the causal relationship corresponding to multiple medical variables at the current time, and the effect node $N_2$ corresponds to the input of the new state at the current time. The causal relationship corresponding to the action node $N_1$ and the effect node $N_2$ is that the action node $N_1$ is activated only when the effect node $N_2$ is "TRUE".

Therefore, differential equations may be used to model structural equations. This differential equation describes how the rate of change in the medical variable corresponding to action node $N_1$ over time is influenced by the medical variable corresponding to effect node $N_2$. The fixed delay between effect node $N_2$ and action node $N_1$ is regarded as a constant in the equation:

$$d(\text{action node})/dt = f3(\text{last state}), \tag{4}$$

its "last state" represents the last state node (e.g., the effect node $N_2$ in FIG. 6). Function $f_3$ describes how the last state affects the rate of change of the medical variable corresponding to action node $N_1$ over time.

The precondition node $N_0$ in FIG. 6 may have multiple states or values, and each state or value represents a specific condition or requirement. These states in the precondition node $N_0$ may correspond to different variable values or configurations that affect activation or selection of action node $N_1$. Depending on the specific state or value of the precondition node $N_0$, different action nodes $N_1$ may be activated or selected. Each action node corresponds to specific subplan information (e.g., the method or technology corresponding to the treatment manner record).

The value of action node $N_1$ in FIG. 6 generally represents the output or decision made by the intervention function/behavior associated with this action node $N_1$. For example, the plan information, subplan information and/or treatment manner records determined in step S220. Intervention behavior determines the specific treatment session plan or actions to be executed according to various factors such as current system state, patient condition, and treatment goals. The value of action node $N_1$ may represent treatment session plan and intervention time. The action node $N_1$ encapsulates the decision made regarding the interference behavior, which includes the specific treatment session plan to be executed and when it should be executed.

The structural equation may express the causal relationship between the action node $N_1$ and the effect node $N_2$. In response to the interference of the exogenous influence EE, the decision of the action node $N_1$ causes the effect node $N_2$ to transition to a new state. This structural equation may be realized through the differential equation:

$$d(\text{next state})/dt = f4(\text{the third period between action node,} \quad (5)$$

$$\text{intervention behavior and effect node}),$$

where $f_4$ describes the change rate of the next state variable as a function of the medical variables and time variables corresponding to the action node.

In a causal graph model, each effect node usually represents a specific result or state of the system. Therefore, each effect node is associated with a value, and this value represents the state or result the system transitions to after executing the intervention behavior. It should be noted that the decision made by the intervention behavior executed on the action node does not directly determine which of the multiple effect nodes to transition to. Effect nodes represent different aspects or results of a treatment, they are usually connected to action nodes and capture the possible consequences of executing the decided treatment manner record. Each effect node may represent a specific treatment result, such as tumor control, normal tissue toxicity, or dose distribution.

In some application scenarios, the initial state/condition may be set arbitrarily, or determined based on prior knowledge or data. In some scenarios, the initial state may not be suitable as a reference for planning decisions, for example, the scenarios where the condition of the patient changes rapidly or the image data quality is poor. In these scenarios, present day automated planning systems may need to rely on other sources of information, such as the medical history of the patient or feedback from the patient or medical staff, to generate an appropriate treatment plan. However, by combining the causal graph model and the intensity matrix, the system does not completely rely on the initial state/condition, but may reflect the current state in real time.

In one application scenario, a tumor of a patient changes in size or shape during treatment. In this scenario, the original treatment plan may no longer be optimal, and a new plan may be needed to address tumor changes. Therefore, new plans need to be generated quickly according to updated information (e.g., medical variables at the current time). However, manual planning may take longer and be error-prone. For example, it is assumed that a patient is initially diagnosed with a small lung tumor, and physicians develop a treatment plan according to the size and location of the tumor. However, during treatment, the tumor continues to grow in size, making the original plan less effective. This new factor in tumor growth may trigger the generation or change of subplans. The embodiment of the disclosure may reevaluate the condition of the patient and generate a new plan that takes into account larger tumor sizes. This new plan may involve adjusting the radiation dose or changing the treatment angle to ensure effective targeting of the tumor while minimizing damage to surrounding healthy tissue. However, if planning is done manually, the process of generating new plans may take longer and be error-prone. Planners need to manually check the latest state of the patient and adjust the plan accordingly. This process may be very time-consuming and not as accurate and efficient as the model inference of the embodiments of the disclosure.

Another embodiment of the disclosure provides a non-transitory computer-readable medium that stores a computer program loaded into a processor to execute each step of the aforementioned plan optimization method (the embodiments shown in FIG. 2 to FIG. 6). This computer program may include multiple program codes, and after the processor 13 loads and executes these program codes, it may complete the above-mentioned plan optimization method and realize the functions of the computing apparatus 10.

To sum up, in the plan optimization method, the computing apparatus for optimizing the plan, and the computer-readable medium of the embodiments of the disclosure, in response to different medical variables, plan information may be determined through machine learning models, and the treatment manner record of the subplan information may be changed accordingly. The period between nodes in the causal graph model is set so that decisions of a plan may reflect the latest variables in a timely manner. In addition, the intensity matrix is defined and the causal relationships between nodes are defined through structural equations. This may improve the accuracy of the model and the efficiency of planning decisions.

Although the disclosure has been described in detail with reference to the above embodiments, they are not intended to limit the disclosure. Those skilled in the art should understand that it is possible to make changes and modifications without departing from the spirit and scope of the disclosure. Therefore, the protection scope of the disclosure shall be defined by the following claims.

What is claimed is:

1. A plan optimization method, comprising:

obtaining a plurality of medical variables at a current time, wherein at least one of the medical variables at the current time is caused by an implementation of medical variables at a previous time with a different value or variable type, and one of the medical variables at the current time corresponds to a state transition from a previous state at the previous time; and determining plan information by inputting the medical variables at the current time into a machine learning model, wherein the plan information comprises at least one subplan information, each of the subplan information corresponds to at least one treatment manner record at a subsequent time, the previous time is earlier than the current time, and the subsequent time is later than the current time, the machine learning model is a causal graph model, and determining the plan information comprises:

determining causal relationships corresponding to the medical variables at the current time through the causal graph model, wherein in response to the at least one of the medical variables at the current time being different from the medical variables at the previous time, generating causal relationships different from that corresponding to the previous time through the causal graph model, and accordingly changing a treatment manner record in at least one subplan information corresponding to the previous time; and setting an intensity matrix, wherein the intensity matrix corresponds to a probability of a state transition of an effect node, an input of the previous state or an input of a new state at the current time corresponds to the state transition, and each of a plurality of elements of the intensity matrix corresponds to an instantaneous rate of the state transition of two states.

2. The plan optimization method according to claim 1, wherein determining the causal relationships corresponding to the medical variables at the current time through the causal graph model comprises:

setting a first period belonging to a first probability distribution, wherein the first period is a period between a precondition node and an action node, the precondition node corresponds to an input of the previous state, the action node is configured to trigger an intervention behavior of the causal relationships corresponding to the medical variables, and the intervention behavior is to change the causal relationships corresponding to the medical variables through the causal graph model;

setting a second period corresponding to the current time and belonging to a second probability distribution, wherein the second period is a delay of the intervention behavior and corresponds to a period from triggering the intervention behavior to actually executing the intervention behavior; and setting a third period belonging to a third probability distribution, wherein the third period is a period between the action node and the effect node, and the effect node corresponds to an input of a new state at the current time.

3. The plan optimization method according to claim 2, wherein the first probability distribution is a delta distribution, the second probability distribution is a gamma distribution, and the third probability distribution is an exponential distribution.

4. The plan optimization method according to claim 1, wherein the instantaneous rate of at least one of the elements in the intensity matrix corresponding to the state transition in which the previous state is a first state corresponds to a period belonging to a probability distribution, the instantaneous rate of at least one of the elements in the intensity matrix corresponding to the state transition in which the previous state is a second state corresponds to transitioning to a new state without executing an intervention behavior, and the instantaneous rate of at least one of the elements in the intensity matrix corresponding to the state transition in which the previous state is a third state corresponds to not executing the intervention behavior while maintaining state.

5. The plan optimization method according to claim 1, wherein determining the causal relationships corresponding to the medical variables at the current time through the causal graph model comprises:

training the causal graph model through a continuous time structural equation model (CTSEM), and determining a causal relationship between a precondition node and an action node, or a causal relationship between the action node and the effect node, wherein the precondition node corresponds to an input of the previous state, the action node is configured to trigger an intervention behavior of causal relationships corresponding to the medical variables, and the effect node corresponds to an input of a new state at the current time.

6. The plan optimization method according to claim 1, wherein obtaining the medical variables at a current time comprises:

obtaining a medical image;
identifying a plurality of objects in the medical image; and grouping the objects according to corresponding treatment effect of the objects to generate a grouping result, wherein the medical variables comprise the grouping result.

7. The plan optimization method according to claim 6, wherein grouping the objects according to the corresponding treatment effect of the objects comprises:

estimating the corresponding treatment effect of each of the objects; and
grouping the estimated treatment effects through a grouping algorithm.

8. The plan optimization method according to claim 7, wherein estimating the corresponding treatment effect of each of the objects comprises:

estimating a conditional average treatment effect (CATE) through a Bayesian structural equation model (BSEM), wherein the conditional average treatment effect is a treatment effect corresponding to one of the object.

9. A computing apparatus used for optimizing a plan, comprising:

a storage, storing program code; and
a processor, coupled to the storage, loading the program code and executing:
obtaining a plurality of medical variables at a current time, wherein at least one of the medical variables at the current time is caused by an implementation of medical variables at a previous time with a different value or variable type, and one of the medical variables at the current time corresponds to a state transition from a previous state at the previous time; and
determining plan information by inputting the medical variables at the current time into a machine learning model, wherein the plan information comprises at least one subplan information, each of the subplan information corresponds to at least one treatment manner record at a subsequent time, the previous time is earlier than the current time, and the subsequent time is later than the current time, the machine learning model is a causal graph model, and determining the plan information comprises:
determining causal relationships corresponding to the medical variables at the current time through the causal graph model, wherein
in response to the at least one of the medical variables at the current time being different from the medical variables at the previous time, generating causal relationships different from that corresponding to the previous time through the causal graph model, and accordingly changing a treatment manner record in at least one subplan information corresponding to the previous time; and
setting an intensity matrix, wherein the intensity matrix corresponds to a probability of a state transition of the effect node, an input of the previous state or an input of a new state at the current time corresponds to the state transition, and each of a plurality of elements of the intensity matrix corresponds to an instantaneous rate of the state transition of two states.

10. The computing apparatus used for optimizing the plan according to claim 9, wherein the processor further executes:

setting a first period belonging to a first probability distribution, wherein the first period is a period between a precondition node and an action node, the precondition node corresponds to an input of the previous state, the action node is configured to trigger an intervention behavior of the causal relationships corresponding to the medical variables, and the intervention behavior is to change the causal relationships corresponding to the medical variables through the causal graph model;

setting a second period corresponding to the current time and belonging to a second probability distribution, wherein the second period is a delay of the intervention behavior and corresponds to a period from triggering the intervention behavior to actually executing the intervention behavior; and setting a third period belonging to a third probability distribution, wherein the third period is a period between the action node and the effect node, and the effect node corresponds to an input of a new state at the current time.

11. The computing apparatus used for optimizing the plan according to claim 10, wherein the first probability distribution is a delta distribution, the second probability distribution is a gamma distribution, and the third probability distribution is an exponential distribution.

12. The computing apparatus used for optimizing the plan according to claim 9, wherein the instantaneous rate of at least one of the elements in the intensity matrix corresponding to the state transition in which the previous state is a first state corresponds to a period belonging to a probability distribution, the instantaneous rate of at least one of the elements in the intensity matrix corresponding to the state transition in which the previous state is a second state corresponds to transitioning to a new state without executing an intervention behavior, and the instantaneous rate of at least one of the elements in the intensity matrix corresponding to the state transition in which the previous state is a third state corresponds to not executing the intervention behavior while maintaining state.

13. The computing apparatus used for optimizing the plan according to claim 9, wherein the processor further executes:

training the causal graph model through a continuous time structural equation model, and determining a causal relationship between a precondition node and an action node, or a causal relationship between the action node and the effect node, wherein the precondition node corresponds to an input of the previous state, the action node is configured to trigger an intervention behavior of causal relationships corresponding to the medical variables, and the effect node corresponds to an input of a new state at the current time.

14. The computing apparatus used for optimizing the plan according to claim 9, wherein the processor further executes:

obtaining a medical image;

identifying a plurality of objects in the medical image; and grouping the objects according to corresponding treatment effect of the objects to generate a grouping result, wherein the medical variables comprise the grouping result.

15. The computing apparatus used for optimizing the plan according to claim 14, wherein the processor further executes:

estimating the corresponding treatment effect of each of the objects; and grouping the estimated treatment effects through a grouping algorithm.

16. A non-transitory computer-readable medium, loading program code through a processor and executing following steps:

obtaining a plurality of medical variables at a current time, wherein at least one of the medical variables at the current time is caused by an implementation of medical variables at a previous time with a different value or variable type, and one of the medical variables at the current time corresponds to a state transition from a previous state at the previous time; and determining plan information by inputting the medical variables at the current time into a machine learning model, wherein the plan information comprises at least one subplan information, each of the subplan information corresponds to at least one treatment manner record at a subsequent time, the previous time is earlier than the current time, and the subsequent time is later than the current time, the machine learning model is a causal graph model, and determining the plan information comprises:

determining causal relationships corresponding to the medical variables at the current time through the causal graph model, wherein in response to the at least one of the medical variables at the current time being different from the medical variables at the previous time, generating causal relationships different from that corresponding to the previous time through the causal graph model, and accordingly changing a treatment manner record in at least one subplan information corresponding to the previous time; and setting an intensity matrix, wherein the intensity matrix corresponds to a probability of a state transition of the effect node, an input of the previous state or an input of a new state at the current time corresponds to the state transition, and each of a plurality of elements of the intensity matrix corresponds to an instantaneous rate of the state transition of two states.

* * * * *